(12) United States Patent
Garrido (10) Patent No.: US 10,188,433 B2
(45) Date of Patent: Jan. 29, 2019

(54) ANTERIOR CERVICAL PLATES FOR SPINAL SURGERY EMPLOYING ANCHOR BACKOUT PREVENTION DEVICES, AND RELATED SYSTEMS AND METHODS

(71) Applicant: Benito J. Garrido, Cornelius, NC (US)

(72) Inventor: Benito J. Garrido, Cornelius, NC (US)

( * ) Notice: Subject to any disclaimer, the term of this patent is extended or adjusted under 35 U.S.C. 154(b) by 38 days.

(21) Appl. No.: 15/205,803

(22) Filed: Jul. 8, 2016

(65) Prior Publication Data
US 2017/0007300 A1 Jan. 12, 2017

Related U.S. Application Data (60) Provisional application No. 62/189,937, filed on Jul. 8, 2015.

(51) Int. Cl.
*A61B 17/80* (2006.01)
*A61B 17/70* (2006.01)
*A61B 17/00* (2006.01)

(52) U.S. Cl.
CPC ...... *A61B 17/7059* (2013.01); *A61B 17/8052* (2013.01); *A61B 2017/00876* (2013.01)

(58) Field of Classification Search
CPC .. A61B 17/808; A61B 17/809; A61B 17/7059
See application file for complete search history.

(56) References Cited

U.S. PATENT DOCUMENTS

| 7,917,223 | B2 | 3/2011 | Madjar et al. | |
|---|---|---|---|---|
| 8,425,395 | B2* | 4/2013 | Kraus | A61B 17/86 600/13 |
| 2004/0049280 | A1* | 3/2004 | Cauthen | A61B 17/1671 623/17.14 |
| 2006/0247633 | A1 | 11/2006 | Winslow et al. | |
| 2007/0179493 | A1* | 8/2007 | Kim | A61B 17/7025 606/33 |
| 2008/0086135 | A1* | 4/2008 | White | A61B 17/7059 606/246 |
| 2011/0319943 | A1* | 12/2011 | Donahoe | A61B 17/7059 606/290 |
| 2012/0226319 | A1* | 9/2012 | Armstrong | A61B 17/7059 606/279 |
| 2015/0251014 | A1 | 9/2015 | Hirschl | |

* cited by examiner

Primary Examiner — Julianna N Harvey
(74) Attorney, Agent, or Firm — Stephen R. Bylciw (57) ABSTRACT

Anterior cervical plates for spinal surgery employing anchor backout prevention devices, and related systems and methods are disclosed. A spinal column includes vertebrae in an articulating structure. Medical intervention may involve limiting the relative motion between vertebrae by fusing at least first and second vertebrae together with osteosynthesis systems. The systems include a plate attached to anterior surfaces of the first and second vertebrae with anchors extending through passageways in the plate. By including one or more anchor backout prevention devices to the plate, movements causing the anchors to disengage from the vertebrae may be avoided. The devices may include a positioning guide, and locking magnets. The implementation of a combination of these devices into the plate may provide greater robustness against failure than any of the devices individually. In this manner, the useful life of the plate within a patient may be lengthened.

20 Claims, 10 Drawing Sheets

ANTERIOR CERVICAL PLATES FOR SPINAL SURGERY EMPLOYING ANCHOR BACKOUT PREVENTION DEVICES, AND RELATED SYSTEMS AND METHODS

CROSS-REFERENCE TO RELATED APPLICATION

This application claims benefit of U.S. Provisional Patent Ser. No. 62/189,937 filed on Jul. 8, 2015 and entitled "Cervical Plate Systems and Method of Use," which is incorporated herein by reference in its entirety.

BACKGROUND

Field of the Disclosure

The technology of the disclosure relates to osteosynthesis systems and related assemblies and methods for connecting bones or portions of bones to each other in an animal, such as a human.

Technical Background

A vertebral column and a spinal cord of a patient extend from the skull to the pelvis and form a longitudinal axis of a patient. The column includes vertebra that are separated by fibrocartilage structures (intervertebral disks) that are interconnected with ligaments. The vertebral column protects the spinal cord and provides structural support for the patient. The spinal cord along with a bundle of nerve fibers extending from the spinal cord form a central nervous system enabling communication between the brain and other parts of the body of the patient. The spinal cord is protected by being disposed within a vertebral canal formed by openings in each of the vertebrae. The vertebral column typically facilitates movement of the patient by enabling relative movement between adjacent vertebrae and often serves its functions without issues, but medical intervention may involve fusing various vertebrae together in a process of stabilization to reduce pain or otherwise facilitate healing or improved quality of life.

In some interventions, anterior cervical plates may be used after an anterior arthrodesis for stabilization purposes. Bone anchors (e.g., bone screws) may be implanted or screwed through anchor passageways in the plates to anchor the anterior cervical plate to vertebrae to immobilize the vertebra with respect to one another. One drawback of conventional anterior cervical plates is that it can be difficult for an attending surgeon to accurately position the anterior cervical plate prior to affixing the anterior cervical plate with the bone anchors and/or maintain the plate in a desired position during the implantation procedure. Bone anchors may also have a tendency to become loose over time, and as a result anterior cervical plates have been designed with various anchor backout prevention mechanisms. These backout prevention mechanisms may be cumbersome resulting in unreliable performance. Further, the mechanisms often involve a multistep engagement process that introduces unnecessary opportunities for error and prolongs the surgery to the detriment of the patient. Accordingly, improvements are needed to better position cervical plates, and to more efficiently and effectively prevent loosening of bone anchors that can uncouple the plates from vertebrae.

SUMMARY OF THE DETAILED DESCRIPTION

Embodiments disclosed herein include anterior cervical plates for spinal surgery employing anchor backout prevention devices, and related systems and methods. A spinal column includes vertebrae in an articulating structure. Medical intervention may involve limiting the relative motion between vertebrae by fusing at least first and second vertebrae together with osteosynthesis systems. The systems include a plate attached to anterior surfaces of the first and second vertebrae with anchors extending through passageways in the plate. By including one or more anchor backout prevention devices to the plate, movements causing the anchors to disengage from the vertebrae may be avoided. The devices may include a positioning guide, and locking magnets. The implementation of a combination of these devices into the plate may provide greater robustness against failure than any of the devices individually. In this manner, the useful life of the plate within a patient may be lengthened.

In this regard, an anterior cervical plate is disclosed having a positioning guide projecting from a rear surface of the plate. The positioning guide is configured such that, when positioned in the space between the first and the second vertebrae and pressed against the first vertebra, the positioning guide positively aligns the bone anchors relative to a corner edge (e.g., anterior corner edge) of the first vertebra. The positive alignment provided by the positioning guide reduces the chance that the plate will slip out of position, for example while the surgeon is awling holes for the bone anchors. The positioning guide facilitates optimal placement of the plate and positively aligns the cephalad anchors (i.e. the anchors nearer the patient's head) close to the corner edge of the first vertebra. This allows the surgeon to select a plate with a smaller vertical extent (i.e. vertical height), maximizing the distance between the top of the plate and the next disc above it, which serves as a mechanism for reducing the chance of adjacent level disc degeneration.

Another embodiment is disclosed that includes an anterior cervical plate incorporating a set of locking magnets providing anchor backout prevention. The locking magnets are magnetically attracted to the heads of the bone anchors. As the bone anchors are inserted through their respective anchor passageways, the locking magnets or mechanism automatically engage with the heads of the anchors to provide resistance to the anchors backing out from the plate and the vertebrae. The engagement of the locking magnets or mechanism with the heads of the anchors is automatic and does not require a separate additional step by the surgeon. Moreover, the locking magnets are preferably incorporated in the plate so as not to add bulk to the exterior profile of the plate. The provision of locking magnets in the anterior cervical plate may also serve to create a low magnetic field within the local bone environment, which can provide a therapeutic fusion benefit. For example, such a local endogenous field has been found to enhance cellular bone differentiation. Electromagnetic fields have also been found to facilitate bony fusion/union in high-risk patients for non-union. Thus, incorporation of locking magnets in the locking mechanism adjacent to the local bone environment may help expedite and/or achieve a higher rate of bony fusion development, thereby increasing the functionality of the plate.

In another embodiment, an anterior cervical plate is disclosed. The anterior cervical plate includes a main body. The main body includes a front surface. The main body also includes a rear surface opposite the front surface, wherein the rear surface is configured to face first and second vertebrae. The main body also includes inner surfaces connected to the front and the rear surfaces, the inner surfaces forming first and second sets of anchor passageways through the main body. The anterior cervical plate also includes a positioning guide projecting from the rear surface and configured such that, when the rear surface abuts against an anterior surface of the first vertebra and the positioning guide abuts against an endplate of the first vertebra, the positioning guide positively aligns the first set of anchor passageways relative to an corner edge of the first vertebra. In this manner, the anterior cervical plate may fuse the vertebrae together while avoiding backout of the anchors from the cervical plate.

In another embodiment, an osteosynthesis system is disclosed. The osteosynthesis system includes an anterior cervical plate including a main body defining first and second anchor passageways and a slot, the slot partially intersecting at least one of the first and the second anchor passageways. The osteosynthesis system further includes first and second anchors disposed in the first and the second anchor passageways. The osteosynthesis system further includes at least one locking magnet disposable in the slot. The at least one locking magnet is confined to the main body and is magnetically attracted to and engages with the first and second anchors so as to resist backout of the first and second anchors from the main body when the first and second anchors are installed in the first and the second anchor passageways. The osteosynthesis system can also include a coil imbedded into the slot that intersects the anchor passageways of which can be externally stimulated to induce an electro-magnetic field for the purposes of bone healing or fusion. In this manner, spinal surgeries can be completed with optimal device placement while ensuring that the anterior cervical plate is secured to the vertebrae with attachments that are strong and stable over time.

In another embodiment, a method is disclosed for installing an anterior cervical plate of an osteosynthesis system. This method may include abutting a rear surface of a main body of an anterior cervical plate against an anterior surface of a first vertebra of adjacent vertebrae, wherein the adjacent vertebrae include the first vertebra and a second vertebra. The method may further include disposing a positioning guide of the anterior cervical plate into a voided space between the adjacent vertebrae. The method may further include pressing the positioning guide against an endplate of the first vertebra to position a first set of anchor passageways of the main body relative to corner edge of the first vertebra. The method may also include securing the main body to the first and the second vertebrae by implanting the first and the second set of anchors of the osteosynthesis system into the first and the second vertebrae and through the first and the second set of anchor passageways. In this manner, anterior cervical plates may be used with dimensions that are smaller than conventional plates to avoid complications for patients.

Additional features and advantages will be set forth in the detailed description which follows, and in part will be readily apparent to those skilled in the art from that description or recognized by practicing the embodiments as described herein, including the detailed description that follows, the claims, as well as the appended drawings.

It is to be understood that both the foregoing general description and the following detailed description present embodiments, and are intended to provide an overview or framework for understanding the nature and character of the disclosure. The accompanying drawings are included to provide a further understanding, and are incorporated into and constitute a part of this specification. The drawings illustrate various embodiments, and together with the description serve to explain the principles and operation of the concepts disclosed.

BRIEF DESCRIPTION OF THE FIGURES

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIGS. 6A-1 and 6A-2 are a front view and a bottom sectional view, respectively, of an exemplary third anterior cervical plate which is a third embodiment of the anterior cervical plate of FIG. 2A, including at least one exemplary locking magnet movable relative to a main body of the third anterior cervical plate, wherein the locking magnets are illustrated in open positions;

FIGS. 6B-1 and 6B-2 are a front view and a bottom sectional view, respectively, of the third anterior cervical plate of FIG. 6A-1, wherein the locking magnets are illustrated in closed positions;

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Reference will now be made in detail to the embodiments, examples of which are illustrated in the accompanying drawings, in which some, but not all embodiments are shown. Indeed, the concepts may be embodied in many different forms and should not be construed as limiting herein; rather, these embodiments are provided so that this disclosure will satisfy applicable legal requirements. Whenever possible, like reference numbers will be used to refer to like components or parts.

Embodiments disclosed herein include anterior cervical plates for spinal surgery employing anchor backout prevention devices and integrated osteosynthesis capacity through electro-magnetic stimulation, and related systems and methods. A spinal column includes vertebrae in an articulating structure. Medical intervention may involve limiting the relative motion between vertebrae by fusing at least first and second vertebrae together with osteosynthesis systems. The systems include a plate attached to anterior surfaces of the first and second vertebrae with anchors extending through passageways in the plate. By including one or more anchor backout prevention devices to the plate, movements causing the anchors to disengage from the vertebrae may be avoided. The devices may include a positioning guide, and locking magnets. The implementation of a combination of these devices into the plate may provide greater robustness against failure than any of the devices individually. In this manner, the useful life of the plate within a patient may be lengthened.

Figure 1A:
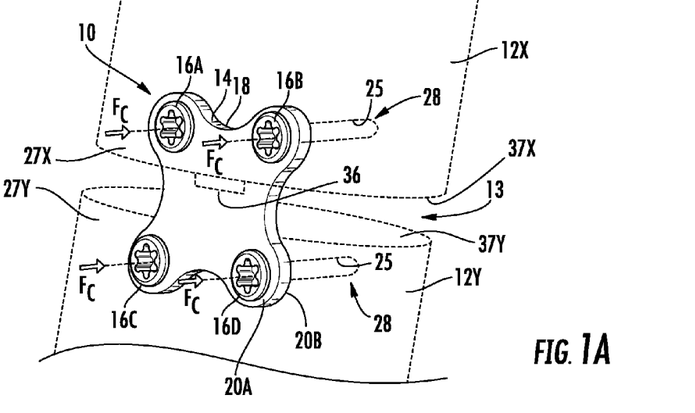
FIGS. 1A through 1D are a top perspective front view, top perspective front exploded view, left side view, and top view of an exemplary osteosynthesis plate system fusing first and second vertebrae together, the system including an exemplary anterior cervical plate, and bone anchors.
Figure 1B:
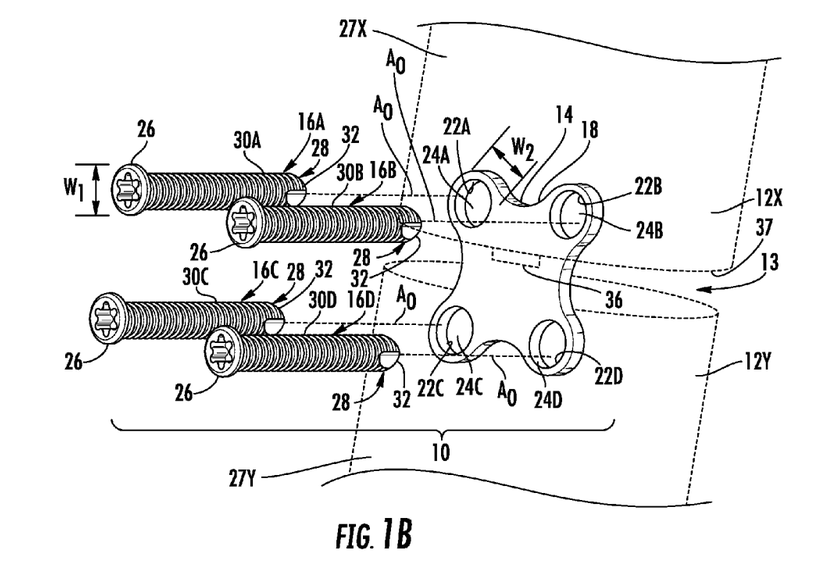
Figure 1C:
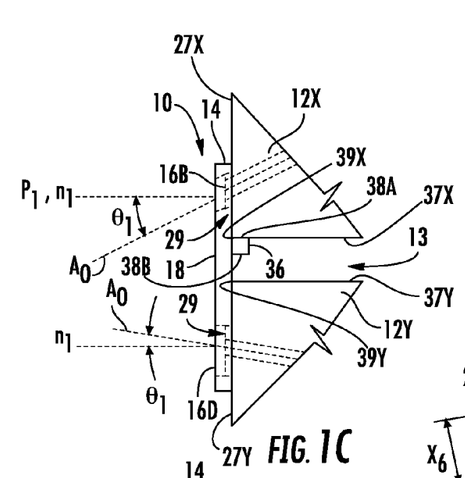
Figure 1D:
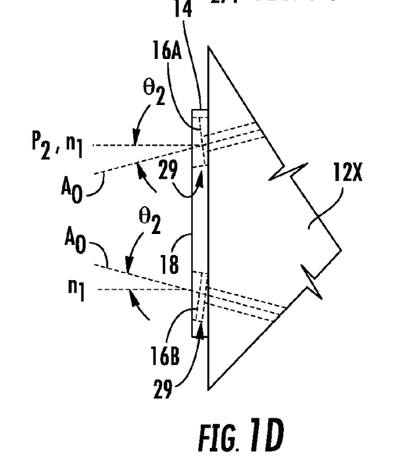
Figure 1E:
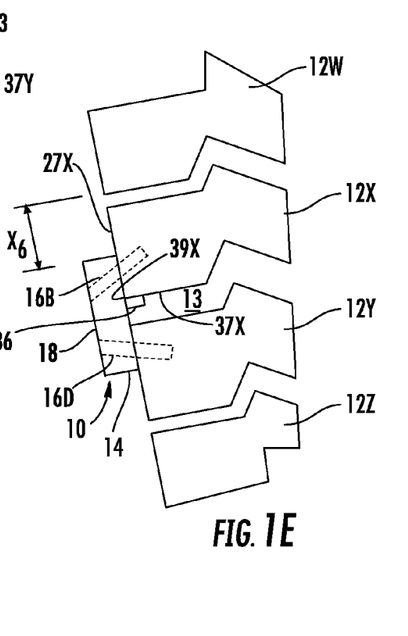
FIG. 1E is a left side view of the osteosynthesis plate system of FIG. 1A illustrating additional vertebrae.

In this regard, FIGS. 1A through 1D are a top perspective front view, top perspective front exploded view, left side view, and top view of an exemplary osteosynthesis plate system 10 fusing first and second vertebrae 12X, 12Y together. Also, FIG. 1E is a left side view of the osteosynthesis plate system 10 of FIG. 1A illustrating additional vertebrae 12W, 12Z. The fusing of the vertebrae 12X, 12Y may occur, for example, for stabilization purposes after an anterior arthrodesis to bridge a discectomy voided space 13 between the first and the second vertebrae 12X, 12Y. The osteosyntesis plate 10 may have several components.

The osteosynthesis plate system 10 may include an anterior cervical plate 14, a first set of bone anchors 16A, 16B, and a second set of bone anchors 16C, 16D. The anterior cervical plate 14 includes a main body 18 with a front surface 20A and a rear surface 20B opposite the front surface 20A. The main body 18 also includes inner surfaces 22A-22D respectively forming anchor passageways 24A-24D extending from the front surface 20A to the rear surface 20B. The bone anchors 16A-16D include heads 26 and distal ends 28 coupled to the heads 26. The heads 26 are configured to interface with an anchor installation tool (e.g., torque driver) and to interface with the main body 18 of the anterior cervical plate 14 while the distal ends 28 are configured to form attachments 25 with the vertebrae 12X, 12Y.

In one embodiment, the bone anchors 16A-16D may respectively include bone screws 30A-30D. The distal ends 28 may include, for example threaded distal ends 32, which are disposed through the anchor passageways 24A-24D (along the center axes A0 of the anchor passageways 24A-24D) and into the first and the second vertebrae 12X, 12Y where they form the attachments 25 with the first and the second vertebrae 12X, 12Y. These attachments 25 are based on at least one of: friction, mechanical interference, cohesive bonds, and adhesive bonds. Also, these attachments 25 resist the withdrawal of the distal ends 28 from the first and the second vertebrae 12X, 12Y and hold or secure the bone anchors 16A-16D in positions stationary relative to the vertebrae 12X, 12Y.

Moreover, a width W1 of the heads 26 is greater than a minimum width W2 of the anchor passageways 24A-24D to enable the heads 26 to form mechanical interferences 29 (FIGS. 1C and 1D) with the main body 18 and thereby prevent the main body 18 from disengaging and backing out from the bone anchors 16A-16D and the first and the second vertebrae 12X, 12Y. After the attachments 25 are formed, the bone anchors 16A-16D may be implanted within the vertebrae 12X, 12Y such that the distal ends 28 are in tension to pull the heads 26 of the bone anchors 16A-16D towards the vertebrae 12X, 12Y and against the anterior cervical plate 14. This pulling of the heads 26 against the anterior cervical plate 14 towards the vertebrae 12X, 12Y holds the anterior cervical plate 14 static against respective anterior surfaces 27X, 27Y of the first and the second vertebrae 12X, 12Y with a force Fc (FIG. 1A).

Figures 2A, 2B:
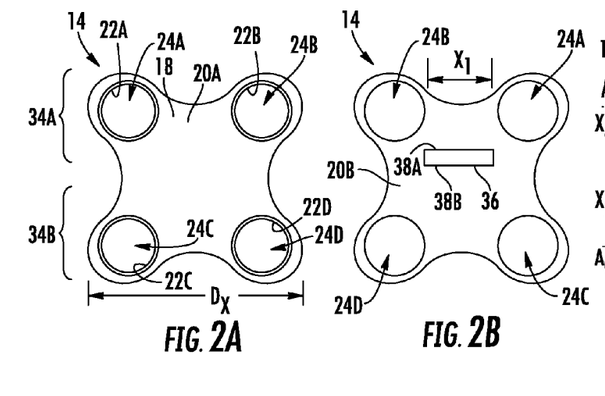
FIGS. 2A through 2C are front, rear and right side views, respectively, of the anterior cervical plate of FIG. 1A, including exemplary dimensions thereof.
Figure 2C:
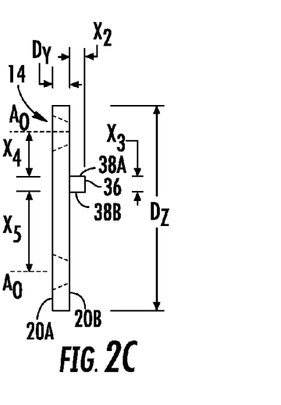

Other details of the anterior cervical plate 14 of FIG. 1A are now provided. FIGS. 2A through 2C are front, rear and right side views, respectively, of the anterior cervical plate 14 of the osteosynthesis plate system 10 according to an embodiment, including exemplary dimensions thereof. The anterior cervical plate 14 also includes a positioning guide 36, and bone anchors 16A-16D. The positioning guide 36 projects from the rear surface 20B of the main body 18. The rear surface 20B may include a plurality of slots 46A, 46B for receiving locking magnets 42A, 42B. The operation of the locking magnets 42A, 42B will be described later relative to FIG. 3A.

The positioning guide 36 may be formed independently and attached to the main body 18 or formed integrally therewith. The positioning guide 36 is sized to fit between adjacent vertebrae 12X, 12Y being fused by the anterior cervical plate 14 (FIG. 1C). The first and the second vertebrae 12X, 12Y may be the C5 and C6 vertebrae. In use, the positioning guide 36 is inserted into a discectomy voided space 13 between the adjacent vertebrae 12X, 12Y and then pressed against the first vertebra 12X (illustrated as C5), so that a first abutment surface 38A of the positioning guide 36 rests or abuts against an endface 37X (e.g., underside) of the first vertebra 12X and the rear surface 20B of the main body 18 rests or abuts against an anterior surface 27X of the first vertebra 12X, as is illustrated in FIG. 1C. In this orientation, the anchor passageways 24A, 24B are aligned so that the bone anchors 16A, 16B passing through the anchor passageways 24A, 24B enter the first vertebra 12X (e.g., C5) a distance X4 (FIG. 2C) from a corner edge 39X (FIG. 1C), for example, an inferior corner edge of the first vertebra 12X. The corner edge 39X is formed by the anterior surface 27X of the first vertebra 12X and the endface 37X of the first vertebra 12X. Thus, the positioning guide 36 may provide a positive stop that positions the anchor passageways 24A, 24B in an ideal location for subsequent insertion or implantation of the bone anchors 16A, 16B into the first vertebra 12X.

Prior to anchor implantation (or insertion), and while the anterior cervical plate 14 is held in the ideal position relative to the first vertebra 12X, the attending surgeon may form pilot holes (not shown) in the first vertebra 12X for the bone anchors 16A, 16B to be implanted by inserting a suitable hole forming instrument, for example, an awl (not shown) or a screw tap (not shown) through the upper anchor passageways 24A, 24B in the main body 18 and into the first vertebra 12X. The positive positioning provided by the positioning guide helps to maintain the anterior cervical plate 14 in position through this process and thereby reduces the chances that the attending surgeon will form the pilot holes in the wrong locations.

It is also noted that the positioning guide 36 may also serve as a backout prevention device for the bone anchors 16A, 16B by helping hold the anterior cervical plate 14 fixed relative to the first vertebra 12X in the case that one of the attachments 25 of the bone anchors 16A, 16B fails. Movement of the anterior cervical plate 14 relative to the first vertebra 12X may cause the remaining attachment 25 of the bone anchors 16A, 16B that has not yet failed to weaken prematurely and the associated bone anchor to backout of the anterior cervical plate 14. In this manner, the positioning guide 36 may prevent backout of the bone anchors.

Moreover, because the anchor passageways 24A, 24B are positively positioned relative to the corner edge 39X of the first vertebra 12X, the attending surgeon does not need to select a size of the anterior cervical plate 14 that mounts the bone anchors 16A, 16B further away from the corner edge 39X of the first vertebra 12X due to the uncertainties of being able to accurately position the bone anchors 16A, 16B any closer to the corner edge 39X. Accordingly, the ability to more precisely position the bone anchors 16A, 16B relative to the first vertebra 12X allows the attending surgeon to select an anterior cervical plate 14 with a smaller vertical extent Dz, and thereby maximize a distance X6 (FIG. 1E) between the anterior cervical plate 14 and a neighboring vertebra 12W (i.e., C4) disposed superior to the adjacent vertebrae 12X, 12Y. Maximizing the distance X6 is advantageous, as smaller values of the distance X6 have been found to be associated with increased chances of adjacent level disc degeneration, or in other words degeneration of the vertebra 12W. Thus, maximizing the distance X6 may reduce the chances of adjacent level disc degeneration or other complications.

With reference back to FIGS. 1C and 1D, the bone anchors 16A, 16B and the bone anchors 16C, 16D may have fixed insertion angle trajectories or, as illustrated, the bone anchors 16A, 16B and the bone anchors 16C, 16D may be variable angle trajectories. Preferably, the bone anchors 16A, 16B and upper anchor passageways 24A, 24B may be designed to accommodate a first insertion angle $\theta_1$ (theta_1) measured as an angular difference within a sagittal plane P2 of the center axis A0 with respect to a vector n1 orthogonal to the main body 18. The first insertion angle $\theta_1$ (theta_1) may be within a range from minus twenty-five (−25) degrees to plus twenty-five (+25) degrees. Further, the bone anchors 16A, 16B and the bone anchors 16C, 16D may also be inserted at second insertion angles $\theta_2$ (theta_2) measured as an angular difference within a transverse plane P2 of the center axis A0 with respect to a vector n1 orthogonal to the main body 18. The second insertion angle $\theta_2$ (theta_2) may be within a range from minus twenty-five (−25) degrees to plus twenty-five (+25) degrees. In this manner, the attending surgeon may select the first and second insertion angles $\theta_1$, $\theta_2$ of the bone anchors 16A, 16B and the bone anchors 16C, 16D to most securely attach the anterior cervical plate 14 to the adjacent vertebrae 12X, 12Y.

Figures 3A, 3B, 3C, 3D, 3E, 4A, 4B, 4C:
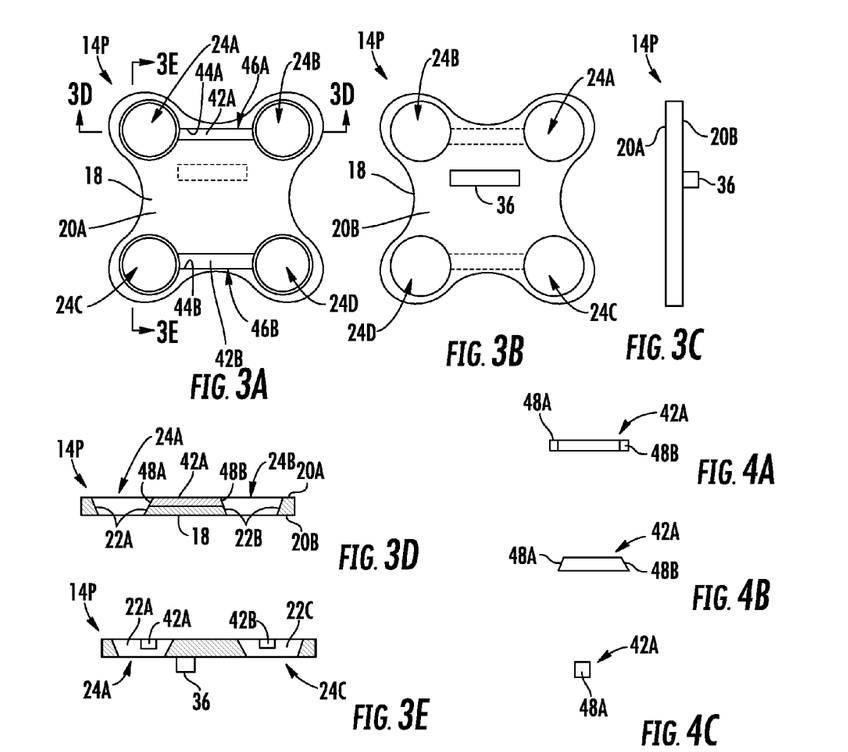
FIGS. 3A through 3E are a front view, a rear view, a right side view, a bottom sectional view, and a left sectional view, respectively, of an exemplary second anterior cervical plate which is a second embodiment of the anterior cervical plate of FIG. 2A, including at least one exemplary locking magnet fixed to the main body of the second anterior cervical plate.
FIGS. 4A through 4C are a top view, a front view, and a left side view of the at least one locking magnet of FIG. 3A.

The osteosynthesis plate system 10 may also include at least one other backout prevention device for the bone anchors 16A, 16B and the bone anchors 16C, 16D. In this regard, FIGS. 3A through 3E are a front view, a rear view, a right side view, a bottom sectional view, and a left sectional view, respectively, of an exemplary second anterior cervical plate 14P that is a second embodiment of the anterior cervical plate 14 of FIG. 2A, including the backout prevention device. This device includes at least one exemplary locking magnet 42A, 42B fixed to the main body 18 of the second anterior cervical plate 14P. In this regard, the anterior cervical plate 14 may include slot surfaces 44A, 44B forming slots 46A, 46B. The locking magnets 42A, 42B are preferably mounted in the slots 46A, 46B in the anterior cervical plate 14 so as to avoid or minimize additional bulk to be added to a side view profile (FIG. 3C) of the anterior cervical plate 14P in comparison to the side view (FIG. 2C) of the anterior cervical plate 14. The slots 46A, 46B and the slot surfaces 44A, 44B may be disposed in the rear surface 20B of the anterior cervical plate 14 (not shown), or in the front surface 20A of the anterior cervical plate 14, as shown in FIG. 3A. The slot 46A intersects with the anchor passageways 24A, 24B and allows magnet ends 48A, 48B of the locking magnet 42A to come in contact with or in close proximity with heads 26 of the bone anchors 16A, 16B. Further, the slot 46B intersects with the anchor passageways 24C, 24D and allows magnet ends 48A, 48B of the locking magnet 42B to come in contact with or in close proximity with heads 26 of the bone anchors 16C, 16D. FIGS. 4A through 4C are a top view, a front view, and a left side view of a non-limiting embodiment of the at least one locking magnet of FIG. 3A.

With continued reference to the embodiment shown in FIGS. 3A through 3E, the locking magnet 42A may fixed in the slot 46A extending between the upper anchor passageways 24A, 24B and the locking magnet 42B is fixed in the slot 46B extending between the lower anchor passageways 24C, 24D. The locking magnets 42A, 42B may be fixed in the slots 46A, 46B in any fashion, for example, such as via a press fit, glue (adhesive or cohesive), soldering, and/or welding. Alternatively the anterior cervical plate 14P may include at least one cover plate (not shown in FIGS. 3A through 3E) attached to the front surface 20A or rear surface 20B of the main body 18 to contain the locking magnets/mechanism 42A, 42B within the slots 43A, 43B without escaping. In these exemplary approaches, the locking magnets 42A, 42B may be attached to the anterior cervical plate 14P.

Figure 5A:
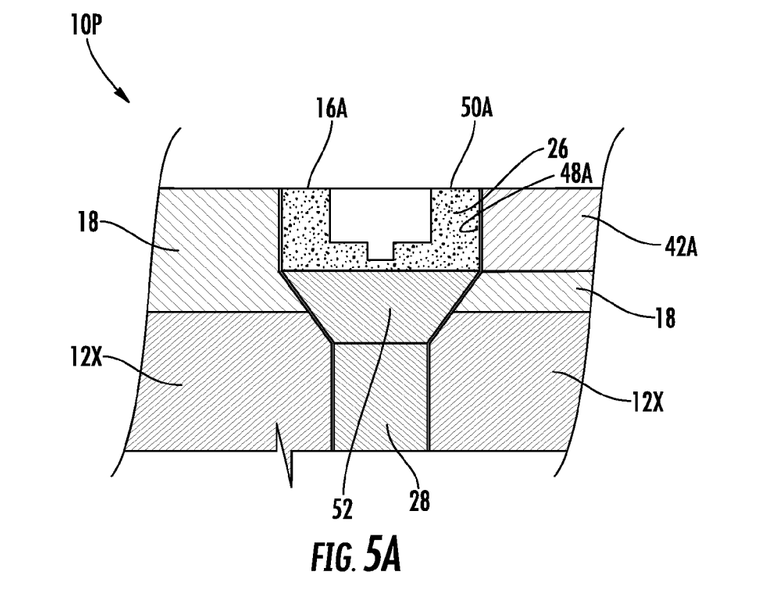
FIGS. 5A and 5B are bottom sectional views of exemplary bone anchors coupled to the second anterior cervical plate of FIG. 3A, wherein outer surfaces of heads of the bone anchors includes linear and curved profiles, respectively.
Figure 5B:
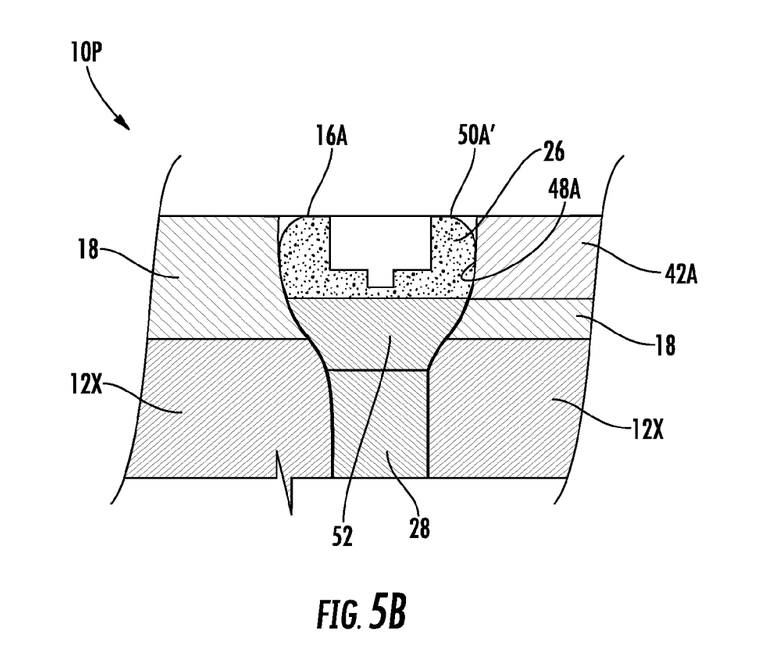

The backout prevention device may be further configured to increase backout protection between the locking magnet 42A and the bone anchors 16A, 16B and between the locking magnet 42B and the bone anchors 16C, 16D. In this regard, FIGS. 5A and 5B are bottom sectional views of exemplary bone anchors coupled to the second anterior cervical plate of FIG. 3A as part of a osteosynthesis plate system 10P, wherein outer surfaces of heads of the bone anchors include linear and curved profiles, respectively. Accordingly, the magnet ends 48A, 48B of the locking magnet 42A may be curved or shaped to match shapes or curvatures 49 of outer surfaces 50A, 50A' of the heads 26 of the bone anchors 16A, 16B, and the heads 26 are magnetized such that the magnet ends 48A, 48B of the locking magnet 42B and the heads 26 are magnetically attracted to each other to prevent backout of the bone anchors 42A-42D from the anterior cervical plate 14P. In operation, as each of the bone anchors 16A, 16B are inserted in the anchor passageways 24A, 24B, the respective one of the heads 26 advances into the anterior cervical plate 14P until meeting one of the magnet ends 48A, 48B of the locking magnet 42A incorporated in the slot 46A in the anterior cervical plate 14P. Similarly, as each of the bone anchors 16C, 16D are inserted in the anchor passageways 24C, 24D, the respective one of the heads 26 advances into the anterior cervical plate 14P until meeting one of the magnet ends 48A, 48B of the locking magnet 42B incorporated in the slot 46B of the anterior cervical plate 14P. Because the locking magnets 42A, 42B are confined or coupled to the slots 46A, 46B of the anterior cervical plate 14P, the magnetic attraction (or magnetic force) between the heads 26 of the bone anchors 16A-16D and at least one of the locking magnets 42A, 42B serves to resist the bone anchors 16A-16D backing out of the anterior cervical plate 14P. In this manner, complications related to the bone anchors 16A-16D desirably uncoupling from the anterior cervical plate 14P may be avoided.

Figure 5C:
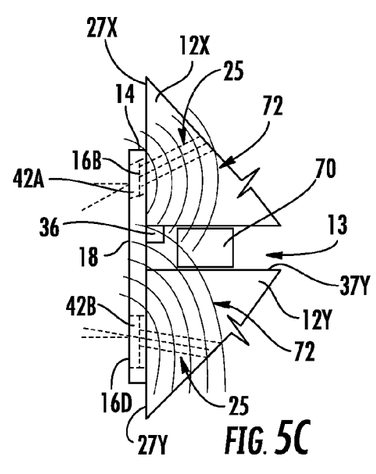
FIG. 5C is a right side view of the anterior cervical plate of FIG. 3A fusing the first and second vertebrae together, wherein the at least one locking magnet creates a magnetic field.

FIG. 5C is a right side view of the anterior cervical plate of FIG. 3A fusing the first vertebra 12X and the second vertebra 12Y together, wherein the locking magnets 42A, 42B creates a magnetic field 72. The magnetic field 72 may be disposed in the attachments 25 of the first vertebra 12X and the second vertebra 12Y to facilitate an acceleration of the healing of the bone tissues to improve the strength of the attachments 25. The magnetic field 72 may also be created to penetrate bone graft material 70 located in the discectomy voided space 13. The magnetic flux 72 created by the locking magnets 42A, 42B may through a process of osteogenesis facilitate an accelerated integration of the bone graft material 70 by the first vertebra 12X and the second vertebra 12Y. In this manner, the first vertebra 12X and the second vertebra 12Y may fuse together quicker and reduce stress on the anterior cervical plate 14.

Figure 5D:
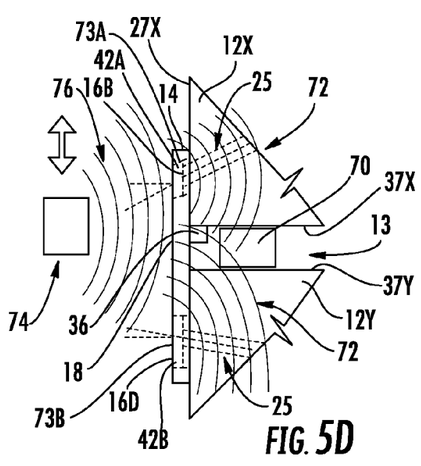
FIG. 5D is a right side view of the anterior cervical plate system of FIG. 3A fusing the first and second vertebrae together, wherein the at least one locking magnet creates a magnetic field under the influence of a stimulator and the at least one locking magnet includes an electromagnet.

The magnetic field 72 may be created differently based on the type of locking magnet used (i.e., permanent magnet and/or electromagnet). FIG. 5D is a right side view of the anterior cervical plate of FIG. 3A fusing the first vertebra 12X and the second vertebrae 12Y together, wherein the locking magnets 42A, 42B create the magnetic field 72 under the influence of a stimulator 74 and the locking magnets 42A, 42B includes at least one electromagnet 73A, 73B. The stimulator 74 may be moved by medical personnel outside the patient and proximate to the locking magnets 42A, 42B including the electromagnets 73A, 73B. The stimulator 74 may create magnetic field 76 that induces the electromagnets 73A to create the magnetic field 72 that may be more precisely located relative to the attachments 25 and the bone graft material 70 than may be conveniently possible with the magnetic field 76 of the stimulator 74. In this manner, the magnetic field 72 may be better directed to facilitate healthy bone formation and development at the attachments 25 and the bone graft material 70.

Figure 5E:
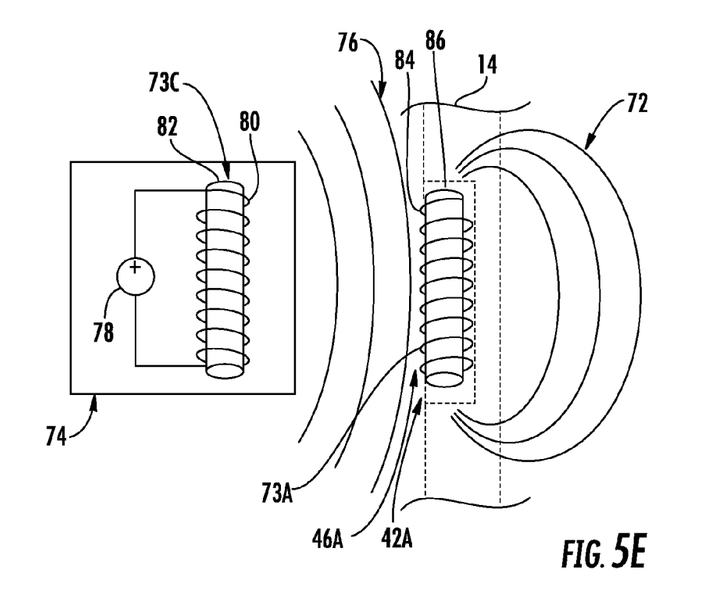
FIG. 5E is a schematic view of the stimulator of FIG. 5D inducing the electromagnet of FIG. 5D to produce the magnetic field.

Details of the stimulator 74 and the electromagnets 73A are now described. FIG. 5E is a schematic view of the stimulator 74 of FIG. 5D inducing in a non-limiting embodiment the electromagnet 73C to produce the magnetic field 76. The stimulator 74 may include components to create static or dynamic magnetic field 76 to induce the electromagnets 73A, 73B fixed to the anterior cervical plate 14P to produce the magnetic field 72. In one embodiment, the stimulator 74 may include the electromagnet 73C powered by a power source 78 (i.e., alternative current power supply). The electromagnet 73C may include a conductive wire 80 wrapped around a metal bar 82. The conductive wire 80 may be coupled to the power source 78 configured to produce an electrical current in the conductive wire 80. Accordingly, a magnetic field 76 is created as the electrical current travels along the conductive wire 80 formed with turns about the metal bar 82. As the stimulator 74 may be placed in proximity to the electromagnets 73A, 73B fixed to the anterior cervical plate 14P, the electromagnets 73A, 73B may produce the magnetic field 72. Each of the electromagnets 73A, 73B may include a conductive wire 84 wrapped around a metal bar 86. Ends of the conductive wire 84 may also in some non-limiting embodiments be coupled to a resistive element (not shown) to form a closed circuit. The electromagnets 73A, 73B may be fixed within the slots 46A, 46B as similarly discussed above with the locking magnets 42A, 42B. Upon receiving the magnetic field 76 from the stimulator 74, a static or dynamic electrical current may be generated in the conductive wire 84 through induction. This electrical current induced in the conductive wires 84 may cause the magnetic field 72 to be created. In this manner, the magnetic field 72 may be created to facilitate osteogenesis of the attachments 25 and the bone graft material 70.

Figure 6A:
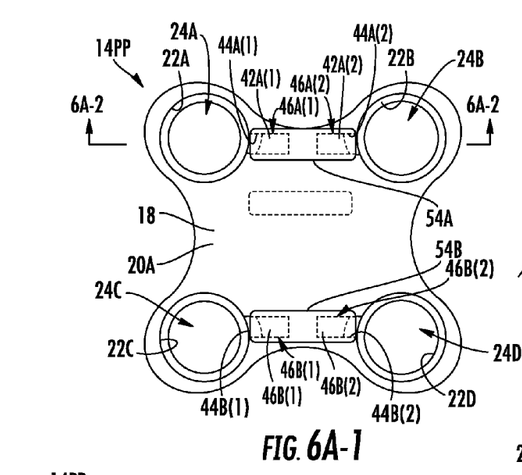
Figure 6A:
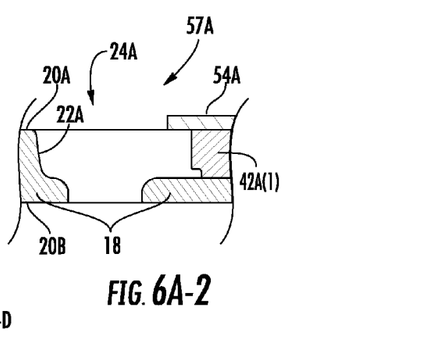
Figure 6B:
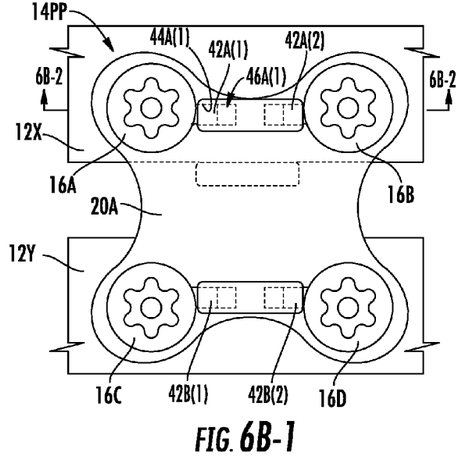
Figure 6B:
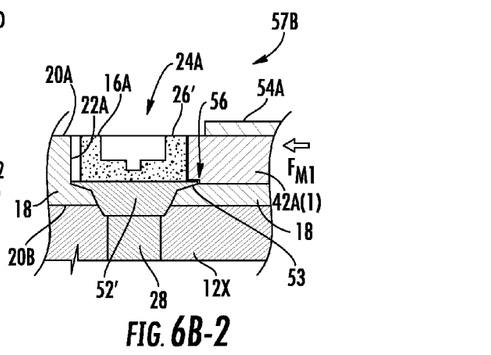

Other embodiments are possible to avoid desirable uncoupling of the bone anchors 16A-16D. FIGS. 6A-1 and 6A-2 are a front view and a bottom sectional view, respectively, of an exemplary third anterior cervical plate 14PP which is a third embodiment of the anterior cervical plate 14 of FIG. 2A. The plate 14PP includes at least one exemplary locking magnet 42A(1), 42A(2), 42B(1), 42B(2) movable relative to the main body 18 of the third anterior cervical plate 14PP, wherein these locking magnets are illustrated in open positions 57A. These locking magnets are translatable (or otherwise movable) within the slots 46A(1), 46A(2), 46B(2), 46B(2) of the anterior cervical plate 14PP, providing a dynamic locking mechanism. Each of the bone anchors 16A-16D includes the head 26 that accommodates a conventional insertion tool (not shown) and a distal end 28 coupled to the head 26. Between the head 26 and the distal end 28, each of the bone anchors 16A-16D defines a circumferential lip 53 coupling the head 26 to the distal end 26. The circumferential lip 53 may be used as one of many interfaces to prevent the desired uncoupling of the bone anchor from the anterior cervical plate 14PP.

Figure 7A:
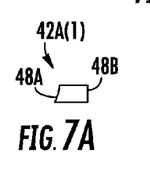
FIGS. 7A through 7C are a front view, a bottom view, and a left side view, respectively, of one of the locking magnets of FIG. 6A-1.
Figure 7B:
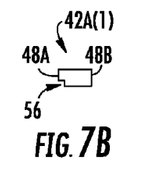
Figure 7C:
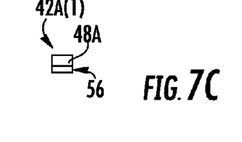

The locking magnets 42A(1), 42A(2), 42B(1), 42B(2) may be used to interface with the circumferential lips 53 of the bone anchors. The locking magnets 42A(1), 42A(2), 42B(1), 42B(2) are confined to the slots 46A(1), 46A(2), 46B(1), 46B(2) by at least one cover plate 54A, 54B (or retention plate), so that these locking magnets can each translate (or move) back and forth within the slots, respectively, as illustrated in FIG. 6A-1. In this regard, the locking magnets 42A(1), 42A(2), 42B(1), 42B(2) translate between an open position 57A that accommodates passage of the circumferential lip 53 away from the anterior cervical plate 14 and a closed position 57B that does not accommodate passage of the circumferential lip 53 from the anterior cervical plate 14. FIGS. 7A through 7C are a front view, a bottom view, and a left side view, respectively, of the locking magnet 42A(1) of FIG. 6A-1. FIGS. 6B-1 and 6B-2 are a front view and a bottom sectional view, respectively, of the third anterior cervical plate of FIG. 6A-1, wherein the locking magnets are illustrated in closed positions 57B. For each of the bone anchors 16A-16D inserted in respective ones of the anchor passageways 24A-24D where the circumferential lips 53 advance past the locking magnets 42A(1), 42A(2), 42B(1), 42B(2), the locking magnets 42A(1), 42A(2), 42B(1), 42B(2) are magnetically attracted to the head 26 or anchor position and at least one of the locking magnets 42A(1), 42A(2), 42B(1), 42B(2) are drawn into contact with each of the heads 26 by virtue of the magnet attraction (magnetic force FM1), bringing the at least one locking magnet 42A(1), 42A(2), 42B(1), 42B(2) into the closed position 57B. With the locking magnets 42A(1), 42A(2), 42B(1), 42B(2) in contact with the heads 26 of the bone anchors 16A-16D, the locking magnets 42A(1), 42A(2), 42B(1), 42B(2) block passages of the circumferential lips 53 (by forming mechanical interferences) and thereby prevent the bone anchors 16A-16D from backing out of the anterior cervical plate 14. If the attending surgeon wishes to allow the bone anchors 16A-16D to back out, the attending surgeon can manually push the locking magnets 42A(1), 42A(2), 42B(1), 42B(2) out of the way of the circumferential lips 53 to allow the bone anchors 16A-16D to be removed (not shown).

Figure 8A:
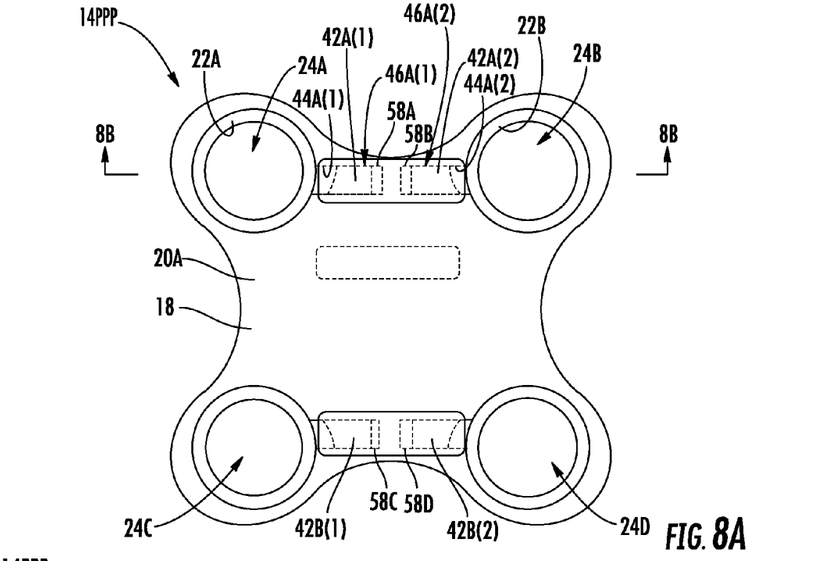
FIGS. 8A and 8B are a front view and a bottom sectional view, respectively, of an exemplary fourth anterior cervical plate which is a fourth embodiment of the anterior cervical plate of FIG. 2A, including at least one exemplary locking magnet movable relative to the main body of the fourth anterior cervical plate and at least one secondary magnet, wherein the locking magnets are illustrated in open positions.
Figure 8B:
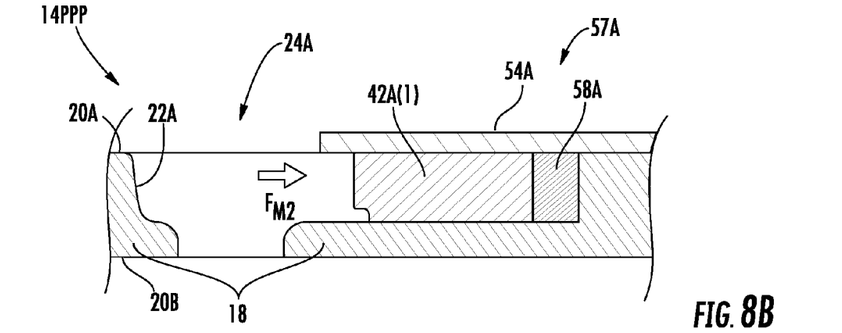
Figure 8C:
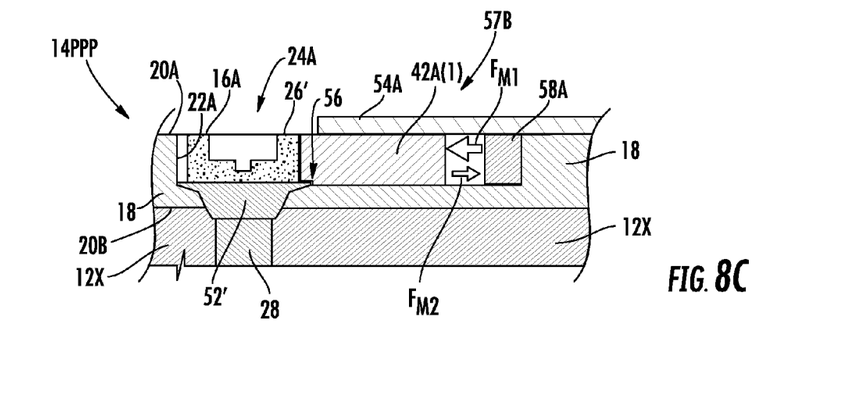
FIG. 8C is a bottom sectional view of the fourth anterior cervical plate of FIG. 8B engaged with a bone anchor, wherein the locking magnet is shown in a closed position coupled to a head of the bone anchor.
Figures 9A, 9B, 9C:
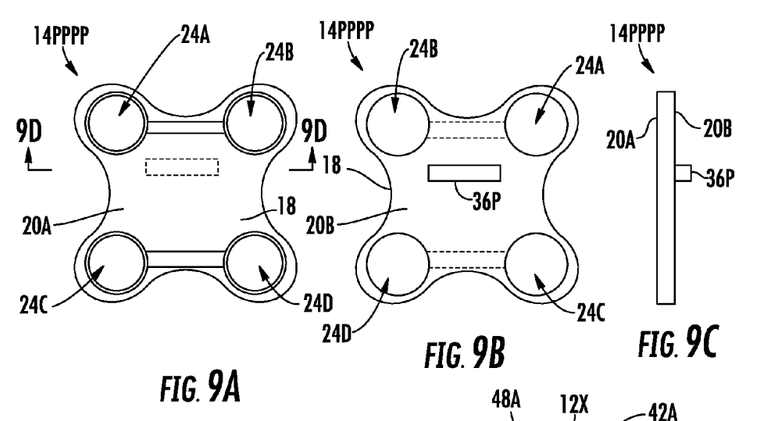
FIGS. 9A through 9D are a front view, a rear view, a right side view, and a sectional view, respectively, of an exemplary fifth anterior cervical plate which is a fifth embodiment of the anterior cervical plate of FIG. 2A.
Figures 9D, 9E:
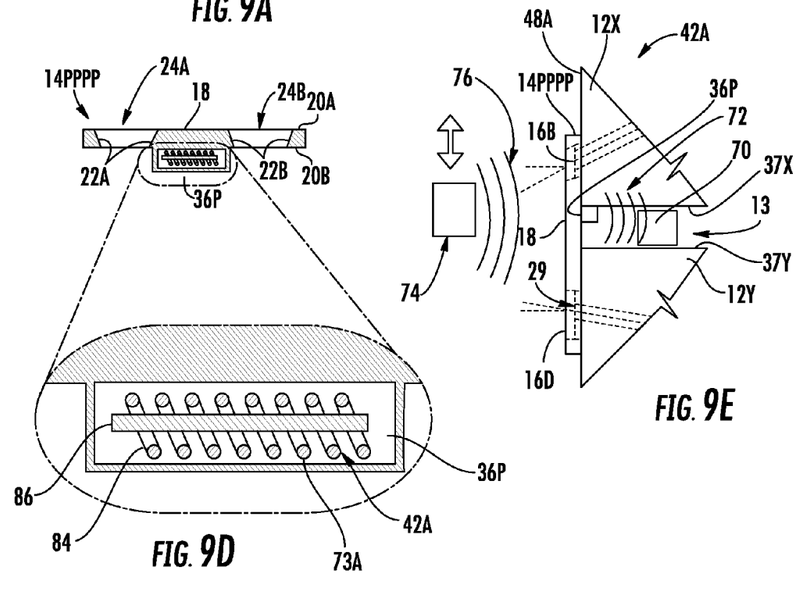
FIG. 9E is a right side view of the anterior cervical plate of FIG. 9A fusing adjacent vertebrae together, wherein the stimulator of FIG. 5D induces an electromagnet to produce the magnetic field.

In another embodiment, the locking magnets 42A(1), 42A(2), 42B(1), 42B(2) may be biased to remain in the open position 57A. In this regard, FIGS. 8A and 8B are a front view and a bottom sectional view, respectively, of an exemplary fourth anterior cervical plate 14PPP which is a fourth embodiment of the anterior cervical plate 14 of FIG. 2A. The fourth anterior cervical plate 14PPP includes the locking magnets 42A(1), 42A(2), 42B(1), 42B(2) movable relative to the main body 18 of the fourth anterior cervical plate 14PPP and at least one secondary magnet 58A-58D, wherein the locking magnets are illustrated in open positions 57A. Accordingly, this biasing may be accomplished by providing the secondary magnets 62A, 62B at opposite ends of the slots 46A, 46B from the anchor passageways 24A-24D. The locking magnets 42A(1), 42A(2), 42B(1), 42B(2) may be weakly attracted to the secondary magnets 58A-58D with a secondary magnetic force FM2. The magnetic force FM1 between an operative end 48A of the each of the locking magnet 42A, 42B and the heads 26 of the bone anchors 16A-16D may be greater than the magnetic force FM2. Thus, the magnetic force FM2 is then strong enough to draw the locking magnets 42A(1), 42A(2), 42B(1), 42B(2) into the closed positions 57B only when the heads 26 of the of the bone anchors 16A-16D has been inserted into the anchor passageways 24A-24D of the anterior cervical plate 14PPP. For example, FIG. 8C is a bottom sectional view of the fourth anterior cervical plate 14PPP of FIG. 8B engaged with the bone anchor 16A, wherein the locking magnet 42A(1) is shown in a closed position 57B and coupled to the head 26' of the bone anchor 16A.

It is to be appreciated in this disclosure that the anterior cervical plate 14 and the locking magnets 42A(1), 42A(2), 42B(1), 42B(2) and the secondary magnets 58A-58D, may include materials appropriate for long-term implantation in a patient 66. For example, the non-magnetic components, such as the anterior cervical plate 14PPP, the distal ends 28 of the bone anchors 16A-16D, and the cover plates 54A, 54B may include titanium. The magnets 42A, 42B and the secondary magnets 58A-58D may include permanent magnets constructed of biocompatible, autoclavable and oxidative resistive alloys. Also, while it is preferred that the anterior cervical plates 14 may incorporate both the positioning guide 36 and the locking magnets 42A(1), 42A(2), 42B(1), 42B(2) described herein, anterior cervical plates 14 are also envisioned that incorporate one or the other. For example, anterior cervical plates 14 using the positioning guide 36 may alternatively utilize any known anchor backout prevention devices, and anterior cervical plates using the locking magnets 42A(1), 42A(2), 42B(1), 42B(2) may be provided with or without the positioning guide 36.

Other embodiments are possible of the anterior cervical plate 14. FIGS. 9A through 9D are a front view, a rear view, a right side view, and a sectional view, respectively, of an exemplary fifth anterior cervical plate 14PPPP which is a fifth embodiment of the anterior cervical plate of FIG. 2A. The anterior cervical plate 14PPPP is similar to the anterior cervical plate 14 of FIG. 2A and so mainly differences will be discussed in the interests of clarity and conciseness. The anterior cervical plate 14PPPP may include the locking magnet 42A embedded within or fixed to the positioning guide 36 to form a positioning guide 36P. The locking magnet 42A may include at least one of a permanent magnet or an electromagnet. In the embodiment illustrated in FIG. 9E, the locking magnet 42A may include the electromagnet 73A including the conductive wire 84 wrapped around the metal bar 86. In this manner, when the electromagnet 73A is placed in the magnetic field 76 of the stimulator 74, then the electromagnet 73A may create a magnetic field 72 proximate to the bone graft material 70, so that formation and generation of tissue in combination with the bone graft material 70 may facilitate the fusing together of the first vertebra 12X and the second vertebra 12Y.

Thus, aside from using locking magnets to prevent bone anchors from backing out of the main body 18 of the anterior cervical plate 14, the locking magnets may also have the ability to generate an electro-magnetic field due to intrinsic properties—ie. functioning as a transducer or through a plate imbedded coil stimulated via an external signal generator (i.e., stimulator 74). Moreover, such an inherent property of such a device/plate or other orthopaedic and or spine implant, rod system, may thus generate an electro-magnetic field to enhance osteogenesis. This may be through an outside or implantable signal generator and be applicable to cervical, anterior lumbar or thoraco-lumbar or other orthopaedic antomically instrumented applications.

Figure 10:
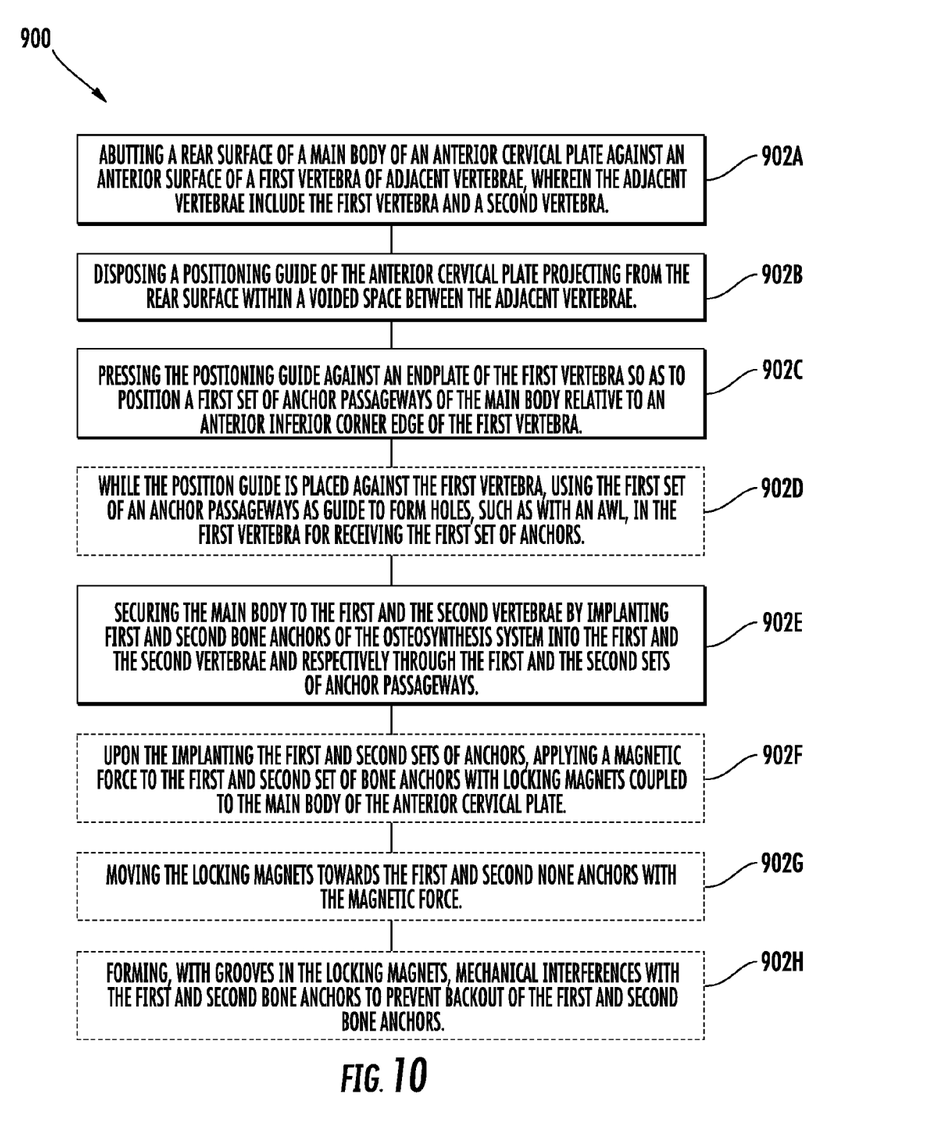
FIG. 10 is a flowchart of an exemplary method of fusing adjacent vertebrae with a osteosynthesis plate system consistent with this disclosure.

FIG. 10 is a flowchart of an exemplary method 900 for fusing the adjacent vertebrae 12X, 12Y during spinal surgery consistent with the osteosynthesis plate systems of disclosed herein. The method 900 is now discussed using the terminology discussed above and below in relation to the operations 902A through 902H as depicted in FIG. 10. In this regard, the method 900 may include abutting a rear surface of a main body of an anterior cervical plate against an anterior surface of a first vertebra of adjacent vertebrae, wherein the adjacent vertebrae include the first vertebra and a second vertebra (operation 902A of FIG. 10). The method may also include disposing a positioning guide of the anterior cervical plate projecting from the rear surface within a voided space between the adjacent vertebrae (operation 902B of FIG. 10). The method may also include pressing the positioning guide against an endplate of the first vertebra so as to position a first set of anchor passageways of the main body relative to an anterior inferior corner edge of the first vertebra (operation 902C of FIG. 10). The method may also include while the position guide is placed against the first vertebra, using the first set of anchor passageways as guides to form holes, such as with an awl, in the upper vertebra for receiving the first set of anchors (operation 902D of FIG. 10). The method may also include securing the main body to the first and the second vertebrae by implanting first and second bone anchors of the osteosynthesis system into the first and the second vertebrae and respectively through the first and the second set of anchor passageways (operation 902E of FIG. 10). The method may also include upon the implanting the first and second set of anchors, applying a magnetic force to the first and second set of bone anchors with locking magnets coupled to the anterior cervical plate. (operation 902F of FIG. 10). The method may also include moving the locking magnets towards the first and second none anchors with the magnetic force. (operation 902G of FIG. 10). The method may also include forming, with grooves in the locking magnets, mechanical interferences with the first and second none anchors. (operation 902H of FIG. 10). In this manner, the vertebrae may be fused while avoiding unwanted decoupling of the plate from the vertebrae.

While described in connection with fusion of vertebra, it is to be understood that an anchor (or screw) backout prevention device using magnets as described herein can be used in other applications. For example, any long bone or high risk for nonunion orthopedic fracture requiring internal fixation with an implant that is secured with bone anchors could benefit from incorporating a magnet lock backout prevention mechanism.

Figure 11A:
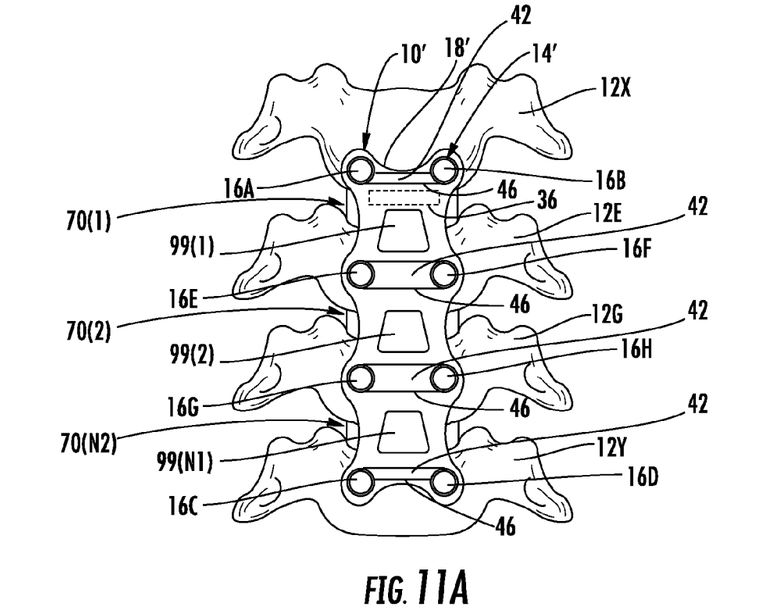
FIGS. 11A and 11B are an anterior view and a right side view, respectively, of an exemplary sixth osteosynthesis plate system including a sixth anterior cervical plate that is a sixth embodiment of the anterior cervical plate of FIG. 2A and may fuse more than two vertebrae together.
Figure 11B:
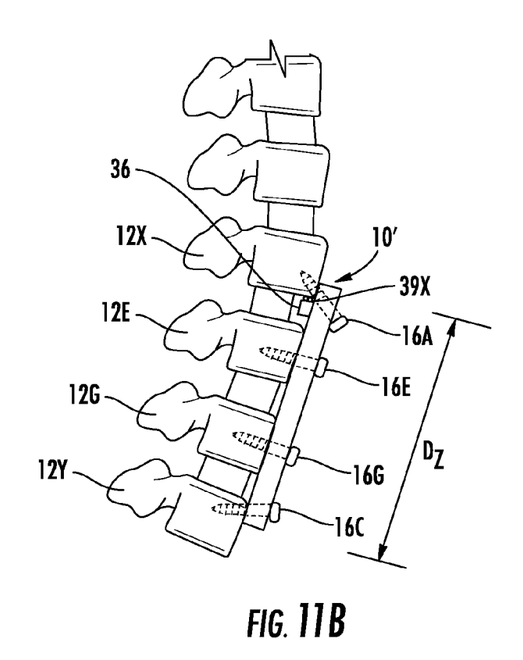

Also, while described in the context of an anterior cervical plate designed for use in securing two vertebras, it is to be understood that the embodiments of this disclosure can be applied to plates used in multi-level fusions, for example securing 3 or 4 vertebrae. FIGS. 11A and 11B are an anterior view and a right side view, respectively, of an exemplary sixth osteosynthesis plate system 10' including a sixth anterior cervical plate 14' that is a sixth embodiment of the anterior cervical plate 14 of FIG. 2A and may fuse more than two vertebrae together. In multilevel degenerative disc disease, multilevel reconstruction, decompression can be performed with instrumentation. With multilevel fusion, inherent nonunion rates have also been described as higher, thus adding magnetic field plate capability may enhance union success. This multi-level version of the plate 14' may be used in the fusion of vertebrae 12X, 12E, 12G, 12Y (for example multiple discs C4-C7). The anterior cervical plate 14' includes the positioning guide 36 projecting from the rear surface 20B that is placed against the anterior inferior corner 39X of the upper most disc being fused, which in this case may be C4. The anterior cervical plate 14' is configured with a vertical extant DZ to span the multiple discs. The anterior cervical plate 14' may include at least one viewing window 99(1)-99(N1). The viewing windows 99(1)-99(N1) include transparent material to enable the attending surgeon to see therethrough for viewing bone grafts 70(1)-70(3) that may be placed or installed between the vertebrae 12X, 12E, 12G, 12Y to be fused in the conventional fashion. Bone anchors 16A-16H (e.g., bone screws) secure the anterior cervical plate 14' to each level, and disposed between each set of the bone anchors 16A-16H of a level, one or more locking magnets 42 and perhaps also secondary magnets (not shown) are provided in one or more slots 46 (or channels) in the main body 18' of the anterior cervical plate 14' to lock the bone anchors 16A-16H in position, as described similarly above to prevent backout of the bone anchors 16A-16H from the main body 18'.

Many modifications and other embodiments not set forth herein will come to mind to one skilled in the art to which the embodiments pertain having the benefit of the teachings presented in the foregoing descriptions and the associated drawings. Therefore, it is to be understood that the description and claims are not to be limited to the specific embodiments disclosed and that modifications and other embodiments are intended to be included within the scope of the appended claims. It is intended that the embodiments cover the modifications and variations of the embodiments provided they come within the scope of the appended claims and their equivalents. Although specific terms are employed herein, they are used in a generic and descriptive sense only and not for purposes of limitation.

What is claimed is:

1. An anterior cervical plate, comprising:
a main body including
a front surface,
a rear surface opposite the front surface, wherein the rear surface is configured to face first and second vertebrae, and
inner surfaces connected to the front and the rear surfaces, wherein the inner surfaces form a first anchor passageway and a second anchor passageway through the main body, wherein the first and the second anchor passageways are configured to respectively receive first and second anchors; and
a positioning guide projecting from the rear surface and configured such that, when the rear surface abuts against an anterior surface of the first vertebra and the positioning guide abuts against an endplate of the first vertebra, the positioning guide positively aligns the first anchor passageway relative to a corner edge of the first vertebra and the positioning guide is configured to be free from abutment against the second vertebra,
wherein the positioning guide includes a magnet configured to create a magnetic field.

2. The anterior cervical plate of claim 1, wherein the first vertebra is disposed superior to the second vertebra.

3. The anterior cervical plate of claim 1, wherein the positioning guide projects from the rear surface a distance in a range from one (1) millimeter to four (4) millimeters.

4. The anterior cervical plate of claim 1, wherein the positioning guide includes an abutment surface configured to abut against the first vertebra, and the abutment surface includes a width in a range from five (5) millimeters to fifteen (15) millimeters.

5. The anterior cervical plate of claim 1, wherein the positioning guide is disposed between center axes of the first and the second anchor passageways.

6. The anterior cervical plate of claim 1, wherein the magnet includes an electromagnet.

7. The anterior cervical plate of claim 6, wherein the electromagnet includes a conductive wire wrapped around a metal bar.

8. The anterior cervical plate of claim 7, wherein the electromagnet is configured to create the magnetic field upon being placed in a second magnetic field of a stimulator.

9. The anterior cervical plate of claim 1, wherein the positioning guide is integral with the main body.

10. An osteosynthesis system, comprising:
an anterior cervical plate including
a main body comprising
a front surface,
a rear surface opposite the front surface, wherein the rear surface is configured to face first and second vertebrae, and
inner surfaces connected to the front and the rear surfaces, wherein the inner surfaces form a first anchor passageway and a second anchor passageway through the main body; and a positioning guide projecting from the rear surface, wherein the rear surface is configured to abut against an anterior surface of the first vertebra and the positioning guide is configured to abut against an endplate of the first vertebra to positively align the first anchor passageway relative to a corner edge of the first vertebra and the positioning guide is configured to be free from abutment against the second vertebra, wherein the positioning guide includes a magnet configured to create a magnetic field between the first and the second vertebra, and first and second anchors disposed in the first and the second anchor passageways and configured to be implanted into the first and the second vertebrae respectively.

11. The osteosynthesis system of claim 10, wherein the positioning guide is configured to maintain abutment against the first vertebrae to prevent rotation of the main body relative to the first vertebra.

12. The osteosynthesis system of claim 10, wherein the positioning guide is disposed between center axes of the first and the second anchor passageways.

13. The osteosynthesis system of claim 10, wherein the magnet includes an electromagnet.

14. The osteosynthesis system of claim 13, wherein the electromagnet includes a conductive wire wrapped around a metal bar.

15. The osteosynthesis system of claim 14, wherein the electromagnet is configured to create the magnetic field upon being placed in a second magnetic field of a stimulator.

16. The osteosynthesis system of claim 10, wherein the positioning guide is integral with the main body.

17. A method of installing an anterior cervical plate of an osteosynthesis system, comprising:

positively aligning a first anchor passageway of a main body of the anterior cervical plate relative to a corner edge of a first vertebra by abutting a positioning guide of the anterior cervical plate against an endplate of the first vertebra and the positioning guide is free from abutment against a second vertebra while a rear surface of the main body of the anterior cervical plate abuts against an anterior surface of the first vertebra, wherein the rear surface faces the first and the second vertebrae, and the rear surface is opposite a front surface of the main body, wherein inner surfaces of the main body connect the front surface to the rear surface and form the first anchor passageway and a second anchor passageway through the main body;

receiving a first anchor in the first anchor passageway and forming a first attachment with the first vertebra while the first anchor passageway is positively aligned;

receiving a second anchor in the second anchor passageway and forming a second attachment with the second vertebra; and creating a magnetic field with a magnet of the positioning guide, wherein the positioning guide projects from the rear surface.

18. The method of claim 17, wherein the magnetic field is disposed between the first and the second vertebrae.

19. The method of claim 18, wherein the creating includes generating the magnetic field from an electromagnet embedded within the positioning guide.

20. The method of claim 19, wherein the creating further includes placing a conductive wire of the electromagnet in a second magnetic field of a stimulator, wherein the conductive wire is wrapped around a metal bar.

* * * * *